(12) United States Patent
Pazenok et al.

(10) Patent No.: US 9,512,081 B2
(45) Date of Patent: Dec. 6, 2016

(54) PROCESS FOR PREPARING 3,5-BIS(FLUOROALKYL)PYRAZOLE DERIVATIVES FROM α,α-DIHALOAMINES

(71) Applicant: BAYER CROPSCIENCE AKTIENGESELLSCHAFT, Monheim am Rhein (DE)

(72) Inventors: Sergii Pazenok, Solingen (DE); Norbert Lui, Odenthal (DE); Arnd Neeff, Burscheid (DE); Winfried Etzel, Leichlingen (DE); Jean-Pierre Vors, Saint Foy les Lyon (FR); Frederic R. Leroux, Herrlisheim (FR); Gregory Landelle, Schiltigheim (FR); Mark James Ford, Schmitten (DE)

(73) Assignees: BAYER CROPSCIENCE AKTIENGESELLSCHAFT, Monheim am Rhein (DE); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/892,291

(22) PCT Filed: May 19, 2014

(86) PCT No.: PCT/EP2014/060238
§ 371 (c)(1),
(2) Date: Nov. 19, 2015

(87) PCT Pub. No.: WO2014/187773
PCT Pub. Date: Nov. 27, 2014

(65) Prior Publication Data
US 2016/0108000 A1    Apr. 21, 2016

(30) Foreign Application Priority Data
May 22, 2013 (EP) .................... 13356007

(51) Int. Cl.
*C07D 231/14* (2006.01)
*C07D 231/12* (2006.01)
*A01N 43/56* (2006.01)

(52) U.S. Cl.
CPC ............. *C07D 231/12* (2013.01); *A01N 43/56* (2013.01); *C07D 231/14* (2013.01)

(58) Field of Classification Search
None
See application file for complete search history.

(56) References Cited

U.S. PATENT DOCUMENTS

| 7,329,633 | B2 | 2/2008 | Dunkel et al. |
| 7,358,387 | B2 | 4/2008 | Lantzsch et al. |
| 7,521,397 | B2 | 4/2009 | Dunkel et al. |
| 7,939,673 | B2 | 5/2011 | Pazenok et al. |
| 8,350,053 | B2 | 1/2013 | Pazenok et al. |
| 8,592,605 | B2 | 11/2013 | Pazenok et al. |
| 8,629,288 | B2 | 1/2014 | Pazenok et al. |
| 8,759,527 | B2 | 6/2014 | Tsuchiya et al. |
| 9,006,266 | B2 | 4/2015 | Tsuchiya et al. |
| 9,150,565 | B2 | 10/2015 | Tsuchiya et al. |
| 2009/0326242 | A1* | 12/2009 | Pazenok ............. C07D 231/14 548/374.1 |
| 2015/0175598 | A1 | 6/2015 | Tsuchiya et al. |

FOREIGN PATENT DOCUMENTS

| WO | 03070705 A1 | 8/2003 |
| WO | 2005042468 A1 | 5/2005 |
| WO | 2008013925 A2 | 1/2008 |
| WO | 2008022777 A2 | 2/2008 |
| WO | 2009106230 A2 | 9/2009 |
| WO | 2009112157 A1 | 9/2009 |
| WO | 2012025557 A1 | 3/2012 |

OTHER PUBLICATIONS

International Search Report from Corresponding PCT/EP2014/060238, mailed Jun. 24, 2014.
Pashkevich et al., Zhurnal Vsesoyuznogo Khimicheskogo Obshchestva im. D.I. Mendeleeva, 1981, 26(1), pp. 105-107.

* cited by examiner

*Primary Examiner* — Kamal Saeed
(74) *Attorney, Agent, or Firm* — McBee Moore Woodward Vanik IP LLC

(57) ABSTRACT

The present invention relates to a novel process for preparing 3,5-bis(fluoroalkyl)pyrazole derivatives from α,α-dihaloamines.

5 Claims, No Drawings

PROCESS FOR PREPARING 3,5-BIS(FLUOROALKYL)PYRAZOLE DERIVATIVES FROM α,α-DIHALOAMINES

CROSS REFERENCE TO RELATED APPLICATIONS

This application is a §371 National Stage Application of PCT/EP2014/060238, filed 19 May 2014, which claims priority to EP 13356007.8, filed 22 May 2013.

BACKGROUND

Field of the Invention

The present invention relates to a novel process for preparing 3,5-bis(fluoroalkyl)pyrazole derivatives.

Description of Related Art

Polyfluoroalkylpyrazolylcarboxylic acid derivatives and 3,5-bis(fluoroalkyl)pyrazoles are valuable precursors for fungicidal active ingredients (for example WO 2003/070705, WO 2008/013925, WO 2012/025557).

Pyrazolecarboxylic acid derivatives are typically prepared by reacting acrylic acid derivatives having two leaving groups with hydrazines (e.g. WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkyl hydrazines.

3,5-Bis(fluoroalkyl)pyrazoles are prepared by reacting bisperfluoroalkyl diketones (e.g. 1,1,1,5,5,5-hexafluoroacetylacetone) with hydrazines (see Pashkevich et al., Zhurnal Vsesoyuznogo Khimicheskogo Obshchestva im. D. I. Mendeleeva (1981), 26(1), 105-7). The yield is only 27 to 40%. The synthesis, isolation and purification of the polyfluoroalkyl diketones is very complex since the compounds are generally very volatile and highly toxic.

In the light of the prior art described above, it is an object of the present invention to provide a process that does not have the aforementioned disadvantages and hence gives a route to 3,5-bis(fluoroalkyl)pyrazole derivatives in high yields.

SUMMARY

The object described above was achieved by a process for preparing 3,5-bis(fluoroalkyl)pyrazoles of the formula (Ia) and (Ib),

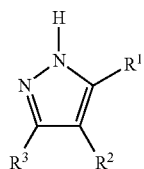

(Ia)

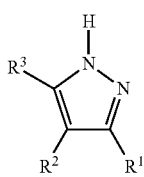

(Ib)

in which $R^1$ and $R^3$ are each independently selected from $C_1$-$C_6$-haloalkyl, optionally halogen substituted $C_1$-$C_6$-alkylphenyl;

$R^2$ is selected from H, halogen, COOH, (C=O)$OR^4$, CN and (C=O)$NR^4R^5$;

$R^4$ and $R^5$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where $R^4$ and $R^5$ together with the nitrogen atom to which they are bonded may form a four-, five- or six-membered ring characterized in that, in step (A), α,α-dihaloamines of the formula (II),

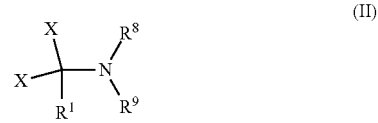

(II)

in which

X is independently selected from F, Cl or Br;

$R^8$ and $R^9$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where $R^8$ and $R^9$ together with the nitrogen atom to which they are bonded may form a five- or six-membered ring;

$R^1$ is as defined above are reacted with compounds of the formula (III),

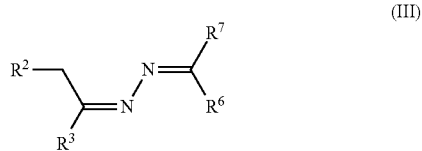

(III)

in which $R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where $R^6$ and $R^7$ together form a five- or six-membered ring;

$R^2$ and $R^3$ are as defined above to form the compound of formula (V)

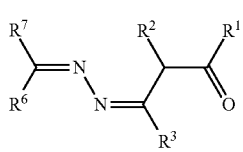

(V)

in which the radicals are as defined above and that in step (B) in the presence of an acid the cyclyzation of (V) takes place.

Preferred is a process according to the invention, where the radicals in formula (Ia), (Ib), (II), (III) and (V) are defined as follows:

$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyl, 1,1,1-trifluoroprop-2-yl, trifluoromethylphenyl, bis(trifluoromethyl)phenyl, fluorophenyl and difluorophenyl;

$R^2$ is selected from H, Br, COOCH$_3$, COOC$_2$H$_5$, COOC$_3$H$_7$, CN, CON(CH$_3$)$_2$ and CON(C$_2$H$_5$)$_2$;

$R^6$, $R^7$ $R^8$ and $R^9$ are each independently selected from H, methyl, ethyl, n- and iso-propyl, n-, iso-, sec- and t-butyl, cyclopropyl, cyclobutyl, cyclopentyl, cyclohexyl, phenyl, benzyl, phenylethyl, C$_{7-19}$-alkylaryl, tolyl, 2,3-, 2,4-, 2,5-, 2,6-, 3,4- or 3,5-dimethylphenyl;

$R^6$ and $R^7$ can also form a 5- or 6-membered ring and

X is independently selected from F or Cl.

More preferred is a process according to the invention, where the radicals in formula (Ia), (Ib), (II), (III) and (V) are defined as follows:

$R^1$ and $R^3$ are each independently selected from difluoromethyl, difluoromethyl, difluorochloromethyl, pentafluoroethyl;

$R^2$ is selected from H, Cl, CN, COOC$_2$H$_5$;

$R^6$, $R^7$ $R^8$ and $R^9$ are each independently selected from, methyl, ethyl, n- and iso-propyl, n-, iso-, sec- and t-butyl, cyclopropyl, phenyl, benzyl, tolyl and X is independently selected from F or Cl.

Even more preferred is a process according to the invention, where the radicals in formula (Ia), (Ib), (II), (III) and (V) are defined as follows:

$R^1$ and $R^3$ are CF$_2$H;

$R^2$ is selected from H or COOC$_2$H$_5$;

$R^6$, $R^7$ $R^8$ and $R^9$ are each independently selected from methyl and phenyl;

X is F.

Most preferred is a process according to the invention, where the radicals in formula (Ia), (Ib), (II), (III) and (V) are defined as follows:

$R^1$ and $R^3$ are CF$_2$H;

$R^2$ is H;

$R^6$ and $R^7$ are phenyl;

$R^8$ and $R^9$ are methyl;

X is F.

DETAILED DESCRIPTION OF A PREFERRED EMBODIMENT

Surprisingly, the pyrazoles of the formula (Ia) and (Ib) can be prepared under the inventive conditions with good yields and in high purity, which means that the process according to the invention overcomes the abovementioned disadvantages of the preparation processes previously described in the prior art.

General Definitions

In the context of the present invention, the term "halogen" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) C$_1$-C$_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl (CF$_3$), difluoromethyl (CHF$_2$), CF$_3$CH$_2$, CF$_2$Cl or CF$_3$CCl$_2$.

Alkyl: groups in the context of the present invention, unless defined differently, are linear, branched or cyclic saturated hydrocarbyl groups. The definition C$_1$-C$_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl: groups in the context of the present invention, unless defined differently, are aromatic hydrocarbyls. The definition C$_{6-18}$-aryl encompasses the widest range defined herein for an aryl group having 6 to 18 skeleton atoms. Specifically, this definition encompasses, for example, the meanings of phenyl, cycloheptatrienyl, cyclooctatetraenyl, naphthyl and anthracenyl.

Arylalkyl groups (aralkyl groups) in the context of the present invention, unless defined differently, are alkyl groups which are substituted by aryl groups and may have one C$_{1-8}$-alkylene chain. The definition C$_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one C$_{1-8}$-alkylene chain. The definition C$_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 1:

Scheme 1:
Step (A):

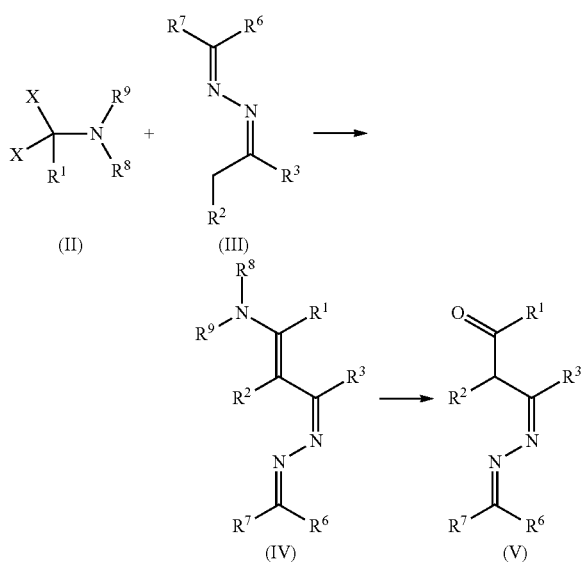

Step (B):

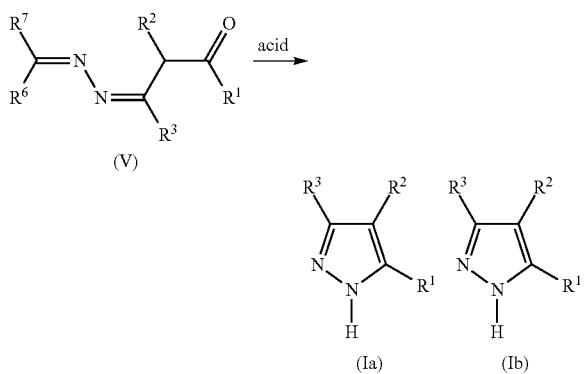

Step (A)

In step (A), α,α-dihaloamines of the formula (II) are first reacted, optionally in the presence of a Lewis acid [L], with compounds of the formula (III).

Preferred compounds of the general formula (II) are 1,1,2,2-tetrafluoroethyl-N,N-dimethylamine (TFEDMA), 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N-diethylamine (Ishikawa's reagent), 1,1,2-trifluoro-2-chloroethyl-N,N-dimethylamine and 1,1,2-trifluoro-2-chloroethyl-N,N-diethylamine (Yarovenko's reagent).

Compounds of the general formula (II) are used as aminofluoroalkylating agents. Preference is given to 1,1,2,2-tetrafluoroethyl-N,N-dimethylamine (TFEDMA) and 1,1,2,2-tetrafluoroethyl-N,N-diethylamine, and particular preference to 1,1,2,2-tetrafluoroethyl-N,N-dimethylamine. α,α-Dihaloamines such as TFEDMA and Ishikawa's reagent are commercially available or can be prepared (cf. Yarovenko et al., Zh. Obshch. Khim. 1959, 29, 2159, Chem. Abstr. 1960, 54, 9724h or Petrov et al., J. Fluor. Chem. 109 (2001) 25-31.

Yagupolskii et al. (Zh. Organicheskoi Khim. (1978), 14(12), 2493-6) shows that the reaction of Yarovenko's reagent (FClCHCF$_2$NEt$_2$) with nitriles of the formula RCH$_2$CN (R is CN or CO$_2$C$_2$H$_5$) affords the derivatives of the formula (NC)RC=C(NEt$_2$)CHFCl in approximately 70% yield. Keto compounds of the formula (III) do not react with α,α-dihaloamines of the formula (II) under these conditions.

Petrov et al. (J. of Fluorine Chem. (2011), 132(12), 1198-1206) shows that TFEDMA (HCF$_2$CF$_2$NMe$_2$) reacts with cyclic β-diketones to transfer a difluoroacetyl group.

In a preferred embodiment the α,α-dihaloamine is first reacted with Lewis acid [L], for example BF$_3$, AlCl$_3$, SbCl$_5$, SbF$_5$, ZnCl$_2$, most preferable BF$_3$ and AlCl$_3$ and then the mixture of the compound of the formula (III) is added in substance or dissolved in a suitable solvent (cf. WO 2008/022777).

α,α-Dihaloamines are reacted with Lewis acids (preparation of the iminium salts of the formula (V) according to the teaching of WO 2008/022777). According to the invention, the reaction is effected at temperatures of −20° C. to +40° C., preferably at temperatures of −20° C. to +30° C., more preferably at −10 to 20° C. and under standard pressure. Due to the hydrolysis sensitivity of the α,α-dihaloamines, the reaction is conducted in anhydrous apparatuses under inert gas atmosphere.

The reaction time is not critical and may, according to the batch size and temperature, be selected within a range between a few minutes and several hours.

According to the invention, 1 mol of the Lewis acid [L] is reacted with equimolar amounts of the α,α-dihaloamine of the formula (II).

For the process according to the invention 1 to 5 mol, preferably 1.5 to 3 mol, more preferably 1.2 to 2 mol of the α,α-dihaloamine of the formula (II) is reacted with 1 mol of the compounds of formula (III).

Preference is given to using compounds of the formula (III) selected from the group comprising Methyl 3-[(diphenylmethylene)hydrazono]-4,4-difluorobutanoate, Ethyl 3-[(diphenylmethylene)hydrazono]-4,4-difluorobutanoate, ethyl 3-[(diphenylmethylene)hydrazono]-4,4,4-trifluorobutanoate, ethyl (3E)-4,4,4-trifluoro-3-(isopropylidenehydrazono)butanoate, ethyl (3E)-4,4,-difluoro-3-(isopropylidenehydrazono)-butanoate, ethyl (3E/3Z)-3-[(2E/2Z)-(4-ethoxy-1,1-difluoro-4-oxobutan-2-ylidene)hydrazono]-4,4,4-trifluorobutanoate, Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, to acetonitrile, THF, Methyl-THF, methyltertbutyl ether or dichloromethane.

The intermediates of the formula (IV) and (V) formed can be used in the cyclization step without prior workup.

Alternatively, the intermediates can be isolated and characterized by suitable workup steps and optionally further purification.

Compounds of formula (III) are new. They can be prepared from aldehydes or ketones (VII) according to the scheme shown below:

Scheme 2:

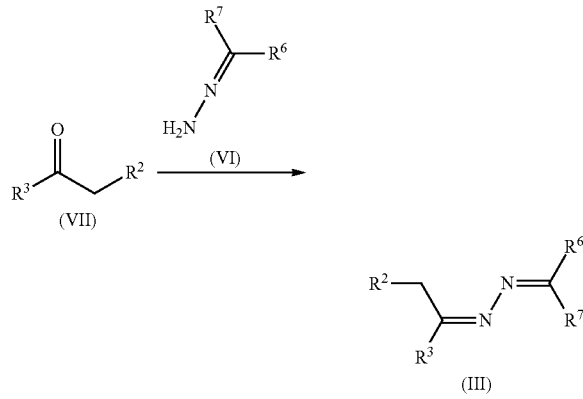

$R^2$, $R^3$, $R^6$ and $R^7$ are as defined above

The reaction of compound (VII) and (VI) according to the invention is effected at temperatures of −40° C. to +120° C., preferably at temperatures of +20° C. to +100° C., more preferably at 20° C. to +60° C. and under standard pressure.

For this process 0.9 to 1.8 mol, preferably 1 to 1.6 mol, most preferably 1 to 1.4 mol of the compound of the formula (VII) is reacted with 1 mol compound of the formula (VI).

It is preferred to have a ratio of 1:1.

The reaction time is not critical and may, according to the batch size and temperature, be selected within a range between a few and many hours. The typical reaction time is 1-5 h.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, alcohols such as methanol, ethanol, isopropanolm butanol. Particular preference is given, for example, to THF, acetonitriles, ethers, toluene, xylene, chlorobenzene, n-hexane, cyclohexane or methylcyclohexane, ethanol and very particular preference, for example, to acetonitrile, THF, ether, dichloromethane, ethanol.

Step (B)

The cyclization in step (B) of the compound of formula (IV) is effected at temperatures of −20° C. to +80° C., preferably at temperatures of −10° C. to +60° C., more preferably at +10° C. to 50° C. and under standard pressure.

The reaction time is not critical and may, according to the batch size, be selected within a relatively wide range.

Typically, the cyclization step (B) is effected without changing the solvent.

Typically the cyclization of compound of the formula (IV) and (V) proceeds under acidic condition.

In many cases it is sufficient to add water to the reaction mixture to perform step B.

After addition of water the reaction mixture usually has a low pH of (1-2), which is important for the elimination of ketones $R^7R^8CO$ and formation of pyrazoles. The amount of water is not crucial for the success of step B.

According to the invention, 0.1 mol to 40 mol, preferably 0.5 to 25 mol of water for 1 mol of the compound of formula (IV) or (V) is used. According to the invention, the reaction is effected at temperatures of −20° C. to +80° C., preferably at temperatures of −10° C. to +60° C., more preferably at +10° C. to 50° C. and under standard pressure. The reaction time is not critical and may, according to the batch size and temperature, be selected within a range between a few minutes and several hours.

It is also possible to use acids.

Preference is given to mineral acids, for example $H_2SO_4$, HCl, $HSO_3Cl$, HF, HBr, HI, $H_3PO_4$ or organic acids, for example CH3COOH, $CF_3COOH$, p-toluenesulphonic acid, methanesulphonic acid, trifluoromethanesulphonic acid.

According to the invention, 0.1 mol to 2 mol, preferably 0.1 to 1.5 mol of the acid for 1 mol of the compound of formula (IV) is used. According to the invention, the reaction is effected at temperatures of −20° C. to +80° C., preferably at temperatures of −10° C. to +60° C., more preferably at +10° C. to 50° C. and under standard pressure. The reaction time is not critical and may, according to the batch size and temperature, be selected within a range between a few minutes and several hours.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (I) where $R^2$ is $COOR^4$ can then be converted to pyrazole acids of the formula (I) $R^2$ COOH.

The conversion is generally performed under acidic or basic conditions.

For acidic hydrolysis, preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$. The reaction can likewise be performed without addition of acid, only in water.

Basic hydrolysis is effected in the presence of inorganic bases such as alkali metal hydroxides, for example lithium hydroxide, sodium hydroxide or potassium hydroxide, alkali metal carbonates, for example $Na_2CO_3$, $K_2CO_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, $Na_2CO_3$ or $K_2CO_3$.

Preference is given to conversion by means of basic hydrolysis.

This reaction is performed preferably within a temperature range from 20° C. to +150° C., more preferably at temperatures of 30° C. to +110° C., most preferably at 30° C. to 80° C. and under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours.

The reaction can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides we dimethylformamide (DMF) or N-methylpyrrolidone (NMP) or mixtures of such solvents, particular preference being given to water, acetonitrile, dichloromethane and alcohols (ethanol).

The inventive compounds (Ia) and (Ib) are used for preparation of active fungicidal ingredients.

EXAMPLES

1. Synthesis of Azines (III-a to III-h)

Benzophenone Hydrazone (VI). A mixture of benzophenone (10 g, 54.9 mmol), hydrazine monohydrate (3.78 mL, 76.8 mmol) and absolute ethanol (20 mL) was refluxed for 12 h. The solvent was removed under reduced pressure and the crude product was recrystallized from absolute ethanol to afford (VI) as white needles (8.78 g, 82%). $^1$H NMR (400 MHz, $CDCl_3$) δ 7.52-7.38 (m, 5H), 7.29-7.20 (m, 5H), 5.42 (br, 2H); $^{13}$C (101 MHz, $CDCl_3$) δ 149.1, 138.5, 133.1, 129.5, 128.9, 128.8, 128.2, 128.1, 126.5; HRMS (ESI) calcd for $C_{13}H_{13}N_2$ [M+H]$^+$ 197.107. found 197.107.

1-(diphenylmethylene)-2-(1,1,1-trifluoropropan-2-ylidene)hydrazine (III-a). A mixture of benzophenone hydrazone (VI) (2 g, 10.2 mmol) and 1,1,1-trifluoroacetone (2.3 mL, 25.5 mmol) was stirred at 40° C. for 12 h. The reaction mixture was diluted in diethyl ether, dried over $Na_2SO_4$, filtrated and concentrated under reduced pressure to remove volatiles. The pure product (III-a) was obtained as a yellow oil (2.93 g, 98%). $^1$H NMR (400 MHz, $CDCl_3$) δ 7.69-7.63 (m, 2H), 7.47-7.33 (m, 6H), 7.21-7.13 (m, 2H), 2.08 (s, 3H); $^{13}$C (101 MHz, $CDCl_3$) δ 159.8, 148.2 (q, $J_{C-F}$=34 Hz), 137.2, 134.0, 132.4, 130.5, 129.5, 128.9, 128.3, 128.1, 120.4 (q, $J_{C-F}$=276 Hz), 12.8; $^{19}$F (376 MHz, $CDCl_3$) δ −72.3 (s, 3F); HRMS (ESI) calcd for $C_{16}H_{14}F_3N_2$ [M+H]$^+$ 291.111. found 291.110.

1-(1,1-difluoropropan-2-ylidene)-2-(diphenylmethylene)hydrazine (III-b). A mixture of benzophenone hydrazone (VI) (320 g, 1.63 mol 1), 1,1-difluoroacetone (185 g L, 1.71 mol) and 0.5 g. p-toluensuphonic acid in 2000 ml of ethanol was stirred at 40° C. for 4 h. 10 g of solid NaHCO3 was added and the mixture stirred for 1 h, filtrated and concentrated under reduced pressure to remove volatiles. The pure (III-b) was obtained as a yellow oil (447 g, 90%) with a purity of 94%). $^1$H NMR (400 MHz, $CDCl_3$) δ 7.70-7.62 (m, 2H), 7.46-7.30 (m, 6H), 7.20-7.10 (m, 2H), 5.92 (t, 1H, J=56 Hz), 2.04 (s, 3H).

1-(1,1-difluoropropan-2-ylidene)-2-(diphenylmethylene)hydrazine (III-b). A mixture of benzophenone hydrazone (VI) (2 g, 10.2 mmol) and 1,1-difluoroacetone (2.07 mL, 25.5 mmol) was stirred at 40° C. for 12 h. The reaction mixture was diluted with diethyl ether, dried over $Na_2SO_4$, filtrated and concentrated under reduced pressure to remove volatiles. The pure product (III-b) was obtained as a yellow oil (2.59 g, 93%). $^1$H NMR (400 MHz, $CDCl_3$) δ 7.70-7.62 (m, 2H), 7.46-7.30 (m, 6H), 7.20-7.10 (m, 2H), 5.92 (t, 1H, J=56 Hz), 2.04 (s, 3H); $^{13}$C (101 MHz, $CDCl_3$) δ 160.1, 154.5 (t, $J_{C-F}$=32 Hz), 137.4, 134.4, 132.4, 130.4, 129.3, 128.8, 128.3, 128.1, 114.4 (t, $J_{C-F}$=239 Hz), 11.0; $^{19}$F (376 MHz, $CDCl_3$) δ −120.1 (d, 2F, J=55 Hz); HRMS (ESI) calcd for $C_{16}H_{14}F_2N_2Na$ [M+Na]$^+$ 295.102. found 295.102.

1-(1-chloro-1,1-difluoropropan-2-ylidene)-2-diphenylmethylene)hydrazine (III-c). A mixture of benzophenone hydrazone (VI) (1 g, 5.09 mmol) and 1-chloro-1,1-difluoroacetone (1.25 mL, 12.7 mmol) was stirred at 40° C. for 12 h. The reaction mixture was diluted with diethyl ether, dried over $Na_2SO_4$, filtrated and concentrated under reduced pressure to remove volatiles. The pure product (III-c) was obtained as a yellow oil (1.52 g, 97%). $^1$H NMR (400 MHz, $CDCl_3$) δ 7.83-7.76 (m, 4H), 7.62-7.54 (m, 2H), 7.51-7.44 (m, 4H), 2.03 (s, 3H); $^{13}$C (75 MHz, $CDCl_3$) δ 196.75, 152.5 (t, $J_{C-F}$=28 Hz), 132.6, 132.4, 130.1, 128.3, 123.0 (t, $J_{C-F}$=289 Hz), 12.5; $^{19}$F (376 MHz, $CDCl_3$) δ −60.1 (s, 2F); HRMS (ESI) calcd for $C_{16}H_{13}ClF_2N_2Na$ [M+Na]$^+$ 329.063. found 329.063.

1-(diphenylmethylene)-2-(3,3,4,4,4-pentafluorobutan-2-ylidene)hydrazine (III-d). A mixture of benzophenone hydrazone (VI) (1 g, 5.09 mmol) and 3,3,4,4,4-pentafluorobutan-2-one (1.6 mL, 12.7 mmol) was stirred at 40° C. for 12 h. The reaction mixture was diluted with diethyl ether, dried over $Na_2SO_4$, filtrated and concentrated under reduced pressure to remove volatiles. The pure product (III-d) was obtained as a yellow oil (1.60 g, 92%). $^1$H NMR (400 MHz, $CDCl_3$) δ 7.70-7.64 (m, 2H), 7.45-7.33 (m, 6H), 7.20-7.12 (m, 2H), 2.09 (s, 3H); $^{13}$C (75 MHz, $CDCl_3$) δ 196.7, 159.8, 148.6 (t, $J_{C-F}$=27 Hz), 137.7, 137.0, 134.1, 132.4, 130.6, 130.1, 129.4, 128.9, 128.6, 128.4, 128.0, 118.7 (qt, $J_{C-F}$=286 Hz, $J_{C-F}$=35 Hz), 110.6 (tq, $J_{C-F}$=254 Hz, $J_{C-F}$=38 Hz), 12.9; $^{19}$F (376 MHz, $CDCl_3$) δ −81.9 (3F), −117.5 (2F); HRMS (ESI) calcd for $C_{17}H_{13}F_5N_2Na$ [M+Na]$^+$ 363.089. found 363.089.

1-(diphenylmethylene)-2-(1-(4-fluorophenyl)ethylidene)hydrazine (III-e). A mixture of benzophenone hydrazone (VI) (1 g, 5.10 mmol), 4-fluoroacetophenone (0.680 mL, 5.61 mmol) and chloroform (1.6 mL) was stirred at room temperature for 48 h. The reaction mixture was diluted with dichloromethane, dried over Na$_2$SO$_4$, filtrated and concentrated under reduced pressure. The crude product was crystallized from pentane to afford (M-e) as yellow needles (1.14 g, 70%). $^1$H NMR (400 MHz, CDCl$_3$) δ 7.78-7.58 (m, 4H), 7.45-7.32 (m, 6H), 7.30-7.22 (m, 2H), 6.98 (t, 2H, J=8.8 Hz), 2.40 (s, 3H); $^{13}$C (101 MHz, CDCl$_3$) δ 164.9, 162.5, 159.1 (d, J$_{C-F}$=219 Hz), 138.3, 135.5, 134.5, 129.8, 129.5, 128.8, 128.6, 128.5, 128.2, 127.8, 115.2 (d, J$_{C-F}$=23 Hz), 15.5; $^{19}$F (376 MHz, CDCl$_3$) δ −111.6 (m, 1F); HRMS (ESI) calculated for C$_{21}$H$_{17}$F$_1$N$_2$Na [M+Na]$^+$ 339.127. found 339.127.

1-(diphenylmethylene)-2-(1-(4-(trifluoromethyl)phenyl) ethylidene)hydrazine (III-f). A mixture of benzophenone hydrazone (VI) (2 g, 10.2 mmol), 4-(trifluoromethyl)acetophenone (2.1 g, 11.2 mmol) and chloroform (3.2 mL) was stirred at room temperature for 48 h. The reaction mixture was diluted with dichloromethane, dried over Na$_2$SO$_4$, filtrated and concentrated under reduced pressure. The crude product was crystallized from pentane to afford (III-f) as yellow needles (3.1 g, 81%). $^1$H NMR (400 MHz, CDCl$_3$) δ 7.78-7.69 (m, 4H), 7.56 (d, 2H, J=8.4 Hz), 7.45-7.35 (m, 6H), 7.28-7.22 (m, 2H), 2.42 (s, 3H); $^{13}$C (101 MHz, CDCl$_3$) δ 159.9, 157.3, 141.5, 138.0, 135.7, 131.1 (q, J$_{C-F}$=33 Hz), 130.0, 129.3, 128.9, 128.8, 128.3, 127.9, 126.9, 125.2 (q, J$_{C-F}$=4 Hz), 121.4 (q, J$_{C-F}$=272 Hz), 15.5; $^{19}$F (376 MHz, CDCl$_3$) δ −62.7 (s, 3F); HRMS (ESI) calcd for C$_{22}$H$_{17}$F$_3$N$_2$Na [M+Na]$^+$ 389.124. found 389.124.

1-(1-(3,5-difluorophenyl)ethylidene)-2-(diphenylmethylene)hydrazine (III-g). A mixture of benzophenone hydrazone (VI) (2 g, 10.2 mmol), 3',5'-difluoroacetophenone (1.75 g, 11.2 mmol) and chloroform (3.2 mL) was stirred at room temperature for 48 h. The reaction mixture was diluted with dichloromethane, dried over Na$_2$SO$_4$, filtrated and concentrated under reduced pressure. The crude product was crystallized from pentane to afford (M-g) as a pale yellow solid (2.72 g, 80%). $^1$H NMR (400 MHz, CDCl$_3$) δ 7.75-7.68 (m, 2H), 7.46-7.34 (m, 6H), 7.25 (m, 2H), 7.18 (m, 2H), 6.78 (m, 1H), 2.37 (s, 3H); $^{13}$C (101 MHz, CDCl$_3$) δ 162.9 (dd, J$_{C-F}$=247 Hz, J$_{C-F}$=13 Hz), 160.3, 156.5, 141.6 (t, J$_{C-F}$=7 Hz), 137.9, 135.2, 130.1, 129.3, 129.0, 128.8, 128.2, 127.9, 109.5 (m), 104.7 (t, J$_{C-F}$=25 Hz), 15.4; $^{19}$F (376 MHz, CDCl$_3$) δ −109.8 (m, 2F); HRMS (ESI) calcd for C$_{21}$H$_{16}$F$_2$N$_2$Na [M+Na]$^+$357.118. found 357.117.

1-(1-(3,5-bis(trifluoromethyl)phenyl)ethylidene)-2-(diphenylmethylene)hydrazine (III-h). A mixture of benzophenone hydrazone (VI) (2 g, 10.2 mmol), 3',5'-bis(trifluoromethyl)acetophenone (2.02 mL, 11.2 mmol) and chloroform (3.2 mL) was stirred at room temperature for 48 h. The reaction mixture was diluted with dichloromethane, dried over Na$_2$SO$_4$, filtrated and concentrated under reduced pressure. The crude product was crystallized from pentane to afford (III-h) as a pale yellow solid (2.7 g, 61%). $^1$H NMR (400 MHz, CDCl$_3$) δ 8.07 (m, 2H), 7.83 (m, 1H), 7.78-7.72 (m, 2H), 7.45-7.37 (m, 6H), 7.29-7.23 (m, 2H), 2.46 (s, 3H); $^{13}$C (101 MHz, CDCl$_3$) δ 161.1, 155.9, 140.2, 137.7, 135.2, 131.7 (q, J$_{C-F}$=32 Hz), 130.3, 129.2, 129.1, 128.9, 128.3, 127.9, 126.6, 123.3 (q, J$_{C-F}$=275 Hz), 122.9, 15.3; $^{19}$F (376 MHz, CDCl$_3$) δ −62.9 (s, 3F); HRMS (ESI) calculated for C$_{23}$H$_{16}$F$_6$N$_2$Na [M+Na]$^+$ 457.111. found 457.111.

2. Synthesis of pyrazoles (Ia/b-a to Ia/b-h)

3,5-bis(difluoromethyl)-1H-pyrazole (Ia/b-b). 300 ml of acetonitrile were placed in a double jacketed flask and cooled to 0° C. AlCl$_3$ 74.4 g (0.553 mol) was added portionwise at this temperature under intensive stirring to form yellow solution. To this mixture a solution of TFEDMA 80 g (0.553 mol) in 350 ml acetonitrile was added at 10° C. to form a yellow suspension. The reaction mixture was stirred for 1 h at room temperature and solution of 114 g (0.395 mol) of 1-(1,1-difluoropropan-2-ylidene)-2-(diphenylmethylene)hydrazine (III-b) in 300 ml acetonitrile was added at 20° C. and the mixture was stirred at 20° C. for 15-18 h. 100 ml water was added slowly to the reaction solution to keep the temperature under 40° C. and the reaction mixture was stirred for 1 h forming two phases mixture. Upper organic layer was separated, washed two times with water, dried over MgSO$_4$ and concentrated in vakuum to give an oily product which consists of (Ia/b-b) and benzophenone. Vacuum distillation at 92-95° C./1 mbar gave 56.4 g (85%) of 3,5-bis(difluoromethyl)-1H-pyrazole (3b) as a white solid with m.p. 70-71° C.

$^1$H NMR (400 MHz, CDCl$_3$) δ 12.5 (br, 1H), 6.77 (t, 2H, T=54.8 Hz), 6.74 (s, 1H);

3-(difluoromethyl)-5-(trifluoromethyl)-1H-pyrazole (Ia/b-a). BF$_3$(OEt$_2$) (0.210 mL, 1.7 mmol) was added to a solution of TFEDMA (0.202 mL, 1.7 mmol) in dry dichloromethane (2 mL) under argon in a teflon flask. The solution was stirred for 15 min at room temperature, and dichloromethane was removed under reduced pressure. The mixture was taken up in dry acetonitrile (2 mL). A solution of (III-a) (0.740 g, 2.5 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over Na$_2$SO$_4$ and evaporated under reduced pressure. The crude material was purified by column chromatography on silica gel with pentane/diethyl ether (100:0 to 60:40) as eluent to afford the pure title compound (Ia/b-a) (0.261 g, 83%) as a pale yellow solid. $^1$H NMR (400 MHz, CDCl$_3$) δ 12.6 (br, 1H), 6.81 (s, 1H), 6.76 (t, 1H, J=54.5 Hz); $^{13}$C (101 MHz, CDCl$_3$) δ 140.7, 128.8, 120.3 (q, J$_{C-F}$=266 Hz), 108.5 (t, J$_{C-F}$=237 Hz), 103.8; $^{19}$F (376 MHz, CDCl$_3$) δ −61.7 (s, 3F), −112.9 (d, 2F, J=54.7 Hz); HRMS (ESI) calculated for C$_5$H$_4$F$_5$N$_2$ [M+H]$^+$ 187.029. found 187.029.

3,5-bis(difluoromethyl)-1H-pyrazole (Ia/b-b). BF$_3$(OEt$_2$) (1.18 mL, 9.55 mmol) was added to a solution of TFEDMA (1.12 mL, 9.55 mmol) in dry dichloromethane (11 mL) under argon in a teflon flask. The solution was stirred for 15 min at room temperature, and dichloromethane was removed under reduced pressure. The mixture was taken up in dry acetonitrile (11 mL). A solution of (III-b) (2.6 g, 9.55 mmol) in acetonitrile (22 mL) was added to the reaction media at room temperature and the mixture was stirred at the same temperature. After 12 h, concentrated hydrochloric acid (2 mL) was added and the reaction was stirred for 1 h at room temperature. Water (50 mL) was added and the solution was extracted with diethyl ether (3×50 mL). The combined organic extracts were washed with brine (50 mL), dried over Na$_2$SO$_4$ and evaporated under reduced pressure. The crude material was purified by column chromatography on silica gel with pentane/diethyl ether (100:0 to 60:40) as eluent to afford the pure title compound (Ia/b-b) (0.950 g, 60%) as a pale yellow solid with m.p. 69-70° C.

$^1$H NMR (400 MHz, CDCl$_3$) δ 12.5 (br, 1H), 6.77 (t, 2H, J=54.8 Hz), 6.74 (s, 1H); $^{13}$C (101 MHz, CDCl$_3$) δ 142.9, 109.3 (t, J$_{C-F}$=236 Hz), 103.2; $^{19}$F (376 MHz, CDCl$_3$) δ −113.2 (d, 4F, J=54.4 Hz); HRMS (ESI) calculated for C$_5$H$_5$F$_4$N$_2$ [1\4+H]$^+$ 169.039. found 169.038.

5-(chlorodifluoromethyl)-3-(difluoromethyl)-1H-pyrazole (Ia/b-c). BF$_3$(OEt$_2$) (0.21 mL, 1.7 mmol) was added to a solution of TFEDMA (0.202 mL, 1.7 mmol) in dry dichloromethane (2 mL) under argon in a teflon flask. The solution was stirred for 15 min at room temperature, and dichloromethane was removed under reduced pressure. The mixture was taken up in dry acetonitrile (2 mL). A solution of (III-c) (0.782 g, 2.55 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over Na$_2$SO$_4$ and evaporated under reduced pressure. The crude material was purified by column chromatography on silica gel with pentane/diethyl ether (100:0 to 60:40) as eluent to afford the pure title compound (Ia/b-c) (0.160 g, 31%) as a pale yellow solid. $^1$H NMR (300 MHz, CDCl$_3$) δ 12.7 (br, 1H), 6.78 (s, 1H), 6.74 (t, 1H, J=54.7 Hz); $^{13}$C (75 MHz, CDCl$_3$) δ 145.5, 141.1, 121.3 (t, J$_{C-F}$=284 Hz), 108.5 (t, J$_{C-F}$=239 Hz), 103.2; $^{19}$F (376 MHz, CDCl$_3$) δ −47.6 (s, 2F), −113.7 (d, 2F, J=54.0 Hz); HRMS (ESI) calculated for C$_5$H$_4$ClF$_4$N$_2$ [M+H]$^+$ 202.999. found 202.998.

3-(difluoromethyl)-5-(perfluoroethyl)-1H-pyrazole (Ia/b-d). BF$_3$(OEt$_2$) (0.21 mL, 1.7 mmol) was added to a solution of TFEDMA (0.202 mL, 1.7 mmol) in dry dichloromethane (2 mL) under argon in a teflon flask. The solution was stirred for 15 min at room temperature, and dichloromethane was removed under reduced pressure. The mixture was taken up in dry acetonitrile (2 mL). A solution of (III-d) (0.868 g, 2.55 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over Na$_2$SO$_4$ and evaporated under reduced pressure. The crude material was purified by column chromatography on silica gel with pentane/diethyl ether (100:0 to 60:40) as eluent to afford the pure title compound (Ia/b-d) (0.310 g, 51%) as a pale yellow solid. $^1$H NMR (300 MHz, CDCl$_3$) δ 12.3 (br, 1H), 6.83 (s, 1H), 6.77 (t, 1H, J=53.9 Hz); $^{13}$C (101 MHz, CDCl$_3$) δ 141.7, 128.3, 118.6 (qt, J$_{C-F}$=285 Hz, J$_{C-F}$=37 Hz), 109.9 (tq, J$_{C-F}$=251 Hz, J$_{C-F}$=40 Hz), 108.4 (t, J$_{C-F}$=239 Hz), 105.1; $^{19}$F (376 MHz, CDCl$_3$) δ −85.0 (s, 3F), −113.4 (s, 2F), −113.8 (d, 2F, J=54.7 Hz); MS (ESI) calculated for C$_6$H$_4$F$_7$N$_2$ [M+H]$^+$ 237.10. found 237.10.

3-(difluoromethyl)-5-(4-fluorophenyl)-1H-pyrazole (Ia/b-e). BF$_3$(OEt$_2$) (0.21 mL, 1.7 mmol) was added to a solution of TFEDMA (0.202 mL, 1.7 mmol) in dry dichloromethane (2 mL) under argon in a teflon flask. The solution was stirred for 15 min at room temperature, and dichloromethane was removed under reduced pressure. The mixture was taken up in dry acetonitrile (2 mL). A solution of (III-e) (0.807 g, 2.55 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over Na$_2$SO$_4$ and evaporated under reduced pressure. The crude material was purified by column chromatography on silica gel with pentane/diethyl ether (100:0 to 50:50) as eluent to afford the pure title compound (Ia/b-e) (0.285 g, 53%) as an off-white solid. $^1$H NMR (400 MHz, CDCl$_3$) δ 12.7 (br, 1H), 7.55-7.45 (m, 2H), 7.12-7.01 (m, 2H), 6.59 (s, 1H), 6.56 (t, 1H, J=54.2 Hz); $^{13}$C (101 MHz, CDCl$_3$) δ 163.2 (d, J$_{C-F}$=253 Hz), 144.9, 127.6 (d, J$_{C-F}$=8 Hz), 125.0, 116.2, 116.1, 110.5 (t, J$_{C-F}$=236 Hz), 100.5; $^{19}$F (376 MHz, CDCl$_3$) δ −111.7 (m, 1F), −112.5 (d, 2F, J=54.4 Hz); HRMS (ESI) calculated for C$_{10}$H$_8$F$_3$N$_2$ [M+H]$^+$ 213.064. found 213.063.

3-(difluoromethyl)-5-(4-(trifluoromethyl)phenyl)-1H-pyrazole (Ia/b-f). BF$_3$(OEt$_2$) (0.21 mL, 1.7 mmol) was added to a solution of TFEDMA (0.202 mL, 1.7 mmol) in dry dichloromethane (2 mL) under argon in a teflon flask. The solution was stirred for 15 min at room temperature, and dichloromethane was removed under reduced pressure. The mixture was taken up in dry acetonitrile (2 mL). A solution of (III-f) (0.935 g, 2.55 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over Na$_2$SO$_4$ and evaporated under reduced pressure. The crude material was purified by column chromatography on silica gel with pentane/diethyl ether (100:0 to 50:50) as eluent to afford the pure title compound (Ia/b-f) (0.280 g, 42%) as a pale yellow solid. $^1$H NMR (400 MHz, CDCl$_3$) δ 12.4 (br, 1H), 7.75-7.55 (m, 4H), 6.76 (s, 1H), 6.66 (t, 1H, J=55.2 Hz); $^{13}$C (101 MHz, CDCl$_3$) δ 144.9, 132.2, 131.2, 130.8, 126.2, 125.8, 123.9 (q, J$_{C-F}$=272 Hz), 110.2 (t, J$_{C-F}$=235 Hz), 101.7; $^{19}$F (376 MHz, CDCl$_3$) δ −62.9 (s, 3F), −112.6 (d, 2F, J=55.0 Hz); HRMS (ESI) calculated for C$_{11}$H$_8$F$_5$N$_2$ [M+H]$^+$ 263.060. found 263.060.

3-(difluoromethyl)-5-(3,5-difluorophenyl)-1H-pyrazole (Ia/b-g). BF$_3$(OEt$_2$) (0.21 mL, 1.7 mmol) was added to a solution of TFEDMA (0.202 mL, 1.7 mmol) in dry dichloromethane (2 mL) under Argon in a Teflon flask. The solution was stirred for 15 min at room temperature, and dichloromethane was removed under reduced pressure. The mixture was taken up in dry acetonitrile (2 mL). A solution of (III-g) (0.853 g, 2.55 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over Na$_2$SO$_4$ and evaporated under reduced pressure. The crude material was purified by column chromatography on silica gel with pentane/diethyl ether (100:0 to 50:50) as eluent to afford the pure title compound (Ia/b-g) (0.180 g, 31%) an off-white solid. $^1$H NMR (400 MHz, CDCl$_3$) δ 13.1 (br, 1H), 7.12-6.93 (m, 2H), 6.82-6.72 (m, 1H), 6.66 (s, 1H), 6.63 (t, 1H, J=54.9 Hz); $^{13}$C (75 MHz, CDCl$_3$) δ 163.6 (dd, J$_{C-F}$=249 Hz, J$_{C-F}$=13 Hz), 144.6, 128.7 (d, J$_{C-F}$=28 Hz), 109.9 (t, J$_{C-F}$=236 Hz), 108.8, 108.5, 104.3 (t, J$_{C-F}$=26 Hz), 101.7; $^{19}$F (376 MHz, CDCl$_3$) δ −108.1 (s, 2F), −113.1 (d, 2F, J=53.5 Hz); HRMS (ESI) calculated for C$_{10}$H$_7$F$_4$N$_2$ [M+H]$^+$ 231.054. found 231.055.

5-(3,5-bis(trifluoromethyl)phenyl)-3-(difluoromethyl)-1H-pyrazole (Ia/b-h). BF$_3$(OEt$_2$) (0.21 mL, 1.7 mmol) was added to a solution of TFEDMA (0.202 mL, 1.7 mmol) in dry dichloromethane (2 mL) under Argon in a Teflon flask. The solution was stirred for 15 min at room temperature, and dichloromethane was removed under reduced pressure. The mixture was taken up in dry acetonitrile (2 mL). A solution of (III-h) (1.1 g, 2.55 mmol) in acetonitrile (4 mL) was added to the reaction media at room temperature and the mixture was heated at 50° C. for 24 h. The reaction mixture was allowed to cool down to room temperature, concentrated hydrochloric acid (0.5 mL) was added and the reaction was stirred for 1 h at the same temperature. Water (10 mL) was added and the solution was extracted with diethyl ether (3×10 mL). The combined organic extracts were washed with brine (10 mL), dried over $Na_2SO_4$ and evaporated under reduced pressure. The crude material was purified by column chromatography on silica gel with pentane/diethyl ether (100:0 to 50:50) as eluent to afford the pure title compound (Ia/b-h) (0.350 g, 42%) as an off-white solid. $^1$H NMR (400 MHz, $CD_3CN$) δ 12.1 (br, 1H), 8.28 (s, 2H), 7.34-7.17 (m, 1H), 7.07 (s, 1H), 6.89 (t, 1H, J=54.6 Hz); $^{13}$C (75 MHz, $CD_3CN$) δ 143.2, 132.9 (q, $J_{C-F}$=39 Hz), 130.1, 129.5, 126.9, 122.8, 124.6 (q, $J_{C-F}$=272 Hz), 111.7 (t, $J_{C-F}$=233 Hz), 103.0; $^{19}$F (376 MHz, $CD_3CN$) δ −63.6 (6F), −113.1 (2F); HRMS (ESI) calculated for $C_{12}H_7F_8N_2$ [M+H]$^+$ 331.048. found 331.048.

Intermediates:
4-[(diphenylmethylene)hydrazono]-1,1,5,5-tetrafluoropent-2-en-2-ol $BF_3(OEt_2)$ (1.18 mL, 9.55 mmol) was added to a solution of TFEDMA (1.12 mL, 9.55 mmol) in dry dichloromethane (11 mL) under argon in a teflon flask. The solution was stirred for 15 min at room temperature, and dichloromethane was removed under reduced pressure. The mixture was taken up in dry acetonitrile (11 mL). A solution of 2b (2.6 g, 9.55 mmol) in acetonitrile (22 mL) was added to the reaction media at room temperature and the mixture was stirred at the same temperature for 12 h. The compound formed was characterized without isolation.

$^1$H NMR (400 MHz, $CDCl_3$) δ 12.6 (s, 1H), 7.78-7.25 (m, 10H), 7.19 (t, 1H, J=54.8 Hz), 5.91 (s, 1H), 5.70 (t, 1H, J=54.8 Hz);
$^{13}$C (101 MHz, $CDCl_3$) δ 187.5 (t, $J_{C-F}$=25 Hz), 156.1, 154.0 (t, $J_{C-F}$=25 Hz), 136.2, 131.3, 130.6, 130.5, 130.0, 128.5, 128.2, 128.1, 110.3 (t, $J_{C-F}$=253 Hz), 108.2 (t, $J_{C-F}$=243 Hz), 86.1; $^{19}$F (376 MHz, $CDCl_3$) δ −123.9 (d, 2F, J=52.6 Hz), −125.2 (d, 2F, J=54.6 Hz);
HRMS (ESI) calculated for $C_{18}H_{14}F_4N_2NaO$ [M+Na]$^+$ 373.093. found 373.09.

The invention claimed is:
1. Process for preparing a 3,5-bis(fluoroalkyl)pyrazole of formula (Ia) and (Ib)

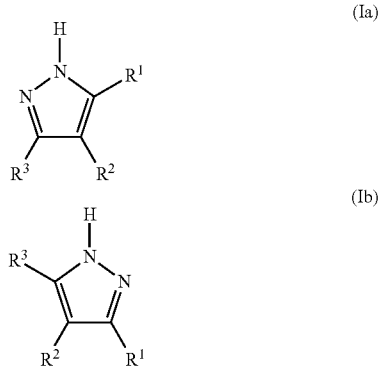

in which
$R^1$ and $R^3$ are each independently selected from $C_1$-$C_6$-haloalkyl, optionally halogen substituted $C_1$-$C_6$-alkylphenyl;
$R^2$ is selected from H, halogen, COOH, (C=O)O$R^4$, CN and (C=O)N$R^4R^5$;
$R^4$ and $R^5$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where
$R^4$ and $R^5$ together with the nitrogen atom to which they are bonded may form a four-, five- or six-membered ring;
comprising reacting, in (A), a α,α-dihaloamine of formula (II),

in which
X is independently selected from F, Cl or Br;
$R^8$ and $R^9$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where
$R^8$ and $R^9$ together with the nitrogen atom to which they are bonded may form a five- or six-membered ring;
$R^1$ is as defined above;
with one or more compounds of formula (III),

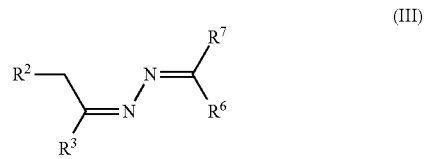

in which
$R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where
$R^6$ and $R^7$ together form a five- or six-membered ring;
$R^2$ and $R^3$ are as defined above
to form the compound of formula (V)

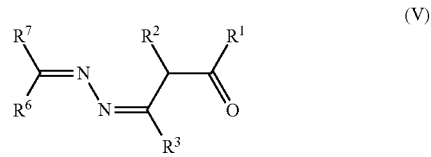

in which the radicals are as defined above
and in (B) in the presence of an acid, a cyclyzation of (V) takes place.
2. Process according to claim 1, wherein
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl, 1,1,1-trifluoroprop-2-yl, trifluoromethylphenyl, bis(trifluoromethyl)phenyl, fluorophenyl and difluorophenyl;

$R^2$ is selected from H, Br, $COOCH_3$, $COOC_2H_5$, $COOC_3H_7$, CN, $CON(CH_3)_2$ and $CON(C_2H_5)_2$;

$R^6$, $R^7$ $R^8$ and $R^9$ are each independently selected from H, methyl, ethyl, n- and iso-propyl, n-, iso-, sec- and t-butyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl;

$R^6$ and $R^7$ can also form a 5- or 6-membered ring and

X is independently selected from F or Cl.

3. Process according to claim 1, wherein $R^1$ and $R^3$ are each independently selected from trifluoromethyl, difluoromethyl, difluorochloromethyl, pentafluoroethyl;

$R^2$ is selected from H, Cl, CN, $COOC_2H_5$;

$R^6$, $R^7$ $R^8$ and $R^9$ are each independently selected from, methyl, ethyl, n- and iso-propyl, n-, iso-, sec- and t-butyl, cyclopropyl, phenyl, benzyl, tolyl and X is independently selected from F or Cl.

4. Process according to claim 1, wherein $R^1$ and $R^3$ are $CF_2H$;

$R^2$ is selected from H or $COOC_2H_5$;

$R^6$, $R^7$ $R^8$ and $R^9$ are each independently selected from methyl and phenyl;

X is F.

5. Process according to claim 1, wherein $R^1$ and $R^3$ are $CF_2H$;

$R^2$ is H;

$R^6$ and $R^7$ are phenyl;

$R^8$ and $R^9$ are methyl;

X is F.

\* \* \* \* \*